United States Patent
Schmidt

(10) Patent No.: US 11,584,813 B2
(45) Date of Patent: Feb. 21, 2023

(54) UNSATURATED MONOMERS AND OLIGOMERS FREE OF PHENOLICS

(71) Applicant: University of Massachusetts, Boston, MA (US)

(72) Inventor: Daniel Frederick Schmidt, Tewksbury, MA (US)

(73) Assignee: University of Massachusetts, Boston, MA (US)

( * ) Notice: Subject to any disclaimer, the term of this patent is extended or adjusted under 35 U.S.C. 154(b) by 288 days.

(21) Appl. No.: 16/488,260

(22) PCT Filed: Mar. 2, 2018

(86) PCT No.: PCT/US2018/020598
§ 371 (c)(1),
(2) Date: Aug. 23, 2019

(87) PCT Pub. No.: WO2018/160930
PCT Pub. Date: Sep. 7, 2018

(65) Prior Publication Data
US 2021/0206893 A1    Jul. 8, 2021

Related U.S. Application Data

(60) Provisional application No. 62/466,217, filed on Mar. 2, 2017.

(51) Int. Cl.
*C08F 122/10* (2006.01)
*C07C 61/35* (2006.01)

(52) U.S. Cl.
CPC ........ *C08F 122/1006* (2020.02); *C07C 61/35* (2013.01)

(58) Field of Classification Search
CPC ................................ C07C 6/135; A61K 6/887
USPC ....................................................... 522/100
See application file for complete search history.

(56) References Cited

U.S. PATENT DOCUMENTS

| | | | |
|---|---|---|---|
| 5,705,575 A | 1/1998 | Kelsey | |
| 7,772,362 B2 | 8/2010 | Beall et al. | |
| 9,139,690 B2 | 9/2015 | Schmidt | |
| 2010/0240794 A1 | 9/2010 | Jin et al. | |
| 2012/0136089 A1 | 5/2012 | Koltisko et al. | |
| 2012/0202920 A1 | 8/2012 | March et al. | |
| 2014/0088289 A1 | 3/2014 | Schmidt | |
| 2016/0115274 A1 | 4/2016 | Kuo et al. | |

FOREIGN PATENT DOCUMENTS

| | | |
|---|---|---|
| CA | 2870875 A1 | 11/2012 |
| EP | 2702029 A1 | 3/2014 |
| WO | WO-2011063172 A2 | 5/2011 |
| WO | WO-2012149340 A1 | 11/2012 |
| WO | WO-2018160930 A1 | 9/2018 |

OTHER PUBLICATIONS

"BPA free dental materials", BPA Free Dental Materials, from the Eco Dentistry Association Greendoc Product Guide, [Online]: Retrieved from the Internet<URL: http://www.ecodentistry.org/?BPA_Free, viewed Feb. 2014>, (2016), 1-3.
"Derakane Momentum™ 411-350 Epoxy Vinyl Ester Resin", Ashland Safety Data Sheet, [Online]. Retrieved from the Internet: <URL: http://www.addresins.co.za/technical-literature/Derakane%20MSDS%20411-350%20EU.pdf.>, (Jan. 23, 2013), 1-16.
"Derakane Momentum™ 411-350 Epoxy Vinyl Ester Resin", Technical Data Sheet, [Online]. Retrieved from the Internet: <URL: http://www.usplastic.com/catalog/files/specsheets/Derakane%20411%20Spec%20Sheet.pdf, viewed Nov. 2016.>, (Nov. 2004), 3 pgs.
"Epoxy Resins Product Overview", [Online]. Retrieved from the Internet: <URL:http://www.dow.com/scripts/litorder.asp?filepath=/296-01683.pdf>, (accessed Mar. 13, 2017), 16 pgs.
"International Application Serial No. PCT/US2018/020598, International Search Report dated May 24, 2018".
"International Application Serial No. PCT/US2018/020598, Written Opinion dated May 24, 2018".
"X-950-0000, BisGMA", ESSTECH, Inc., [Online]. Retrieved from the Internet:<URL:http://catalog.esstechinc.com/item/oligomers/bisgma/x-950-000>, (accessed Mar. 13, 2017), 1.

(Continued)

*Primary Examiner* — Sanza L. McClendon
(74) *Attorney, Agent, or Firm* — Schwegman Lundberg & Woessner, P.A.

(57) ABSTRACT

Various embodiments disclosed relate to a resin having a structure of at least one of Formula I and Formula II: In Formula I or Formula II $R^1$, $R^3$, $R^4$, $R^5$, and $R^6$ can each be independently selected from the group consisting of hydrogen and substituted or unsubstituted $(C_1-C_{10})$alkyl. $R^2$ is $(C_1-C_{10})$ alkylene. L is a substituted or unsubstituted $(C_1-C_{10})$alkylene or $(C_3-C_{10})$cycloalkylene. In Formula I or Formula II, n or m is greater than or equal to 0, and wherein the resin has an average molecular weight of less than 10,000 g/mol.

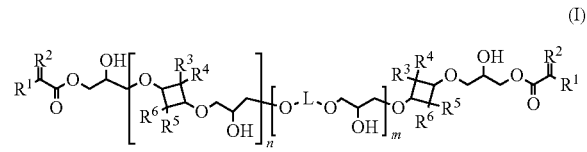

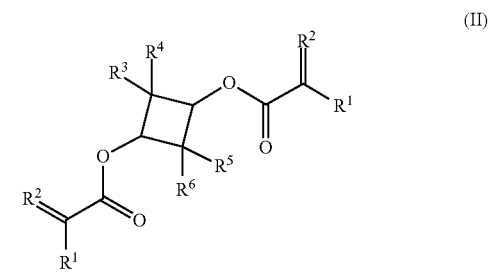

14 Claims, 4 Drawing Sheets

(56) References Cited

OTHER PUBLICATIONS

Campanella, A, et al., "Fatty Acid-Based Comonomers as Styrene Replacements in Soybean and Castor Oil-Based Thermosetting Polymers", Journal of Applied Polymer Science 119 1000-1010 (2011)., (Jan. 2011), 12 pgs.

Campanella, A, et al., "The Use of Acrylated Fatty Acid Methyl Esters as Styrene Replacements in Triglyceride-based Thermosetting Polymers", Polymer Engineering and Science 49 2384-2392 (2009), (Dec. 2009), 12 pgs.

Fleisch, A F, et al., "Bisphenol A and Related Compounds in Dental Materials", Pediatrics 126 760-768 (2010)., [Online]: Retrieved from the Internet:<URL:/content/early/2010/09/06/peds.2009-2693>, (Sep. 6, 2010), 11 pgs.

La Scala, J J, et al., "Fatty acid-based monomers as styrene replacements for liquid molding resins", Polymer 45 7729-8837 (2004)., (May 2006), 16 pgs.

Labauve, J R, et al., "What every dentist should know about bisphenol A", General Dentistry 60 424-432 (2012)., (Jan. 9, 2012), 424-432.

Lin, J, et al., "Use of allyl-functional benzoxazine monomers as replacement for styrene in vinyl ester resins", Polymer International 62 71-78 (2012)., (Jun. 13, 2012), 9 pgs.

Poillucci, R A, et al., "Reducing Use of Styrene Monomer in Unsaturated Polyester Resins", TURI Technical Report 74 (2013, [Online]. Retrieved from the Internet;<URL: http://www.turi.org/content/download/8450/141442/file/2013%20Report%2074%20Hansen%20-%20Safer%20Alternatives%20to%20Styrene%20Polyester.pdf>, (Jun. 2013), 23 pgs.

Söderholm, K J, et al., "Bis-GMA-based Resins in Dentistry: Are They Safe?", Journal of the American Dental Association 130 201-209 (1999)., (Feb. 1999), 201-209.

Yoshii, E, "Cytotoxic effects of acrylates and methacrylates: Relationships of monomer structures and cytotoxicity", Journal of Biomedical Materials Research 37 517-524 (1997)., (Dec. 12, 1996), 8 pgs.

UNSATURATED MONOMERS AND OLIGOMERS FREE OF PHENOLICS

CLAIM OF PRIORITY

This patent application is a U.S. National Stage Filing under 35 U.S.C. § 371 from International Application No. PCT/US2018/020598, filed Mar. 2, 2018, which claims the benefit of priority to U.S. Provisional Application Ser. No. 62/466,217, filed Mar. 2, 2017, which are incorporated by reference herein in their entireties.

BACKGROUND

Cured compositions are widely used for many different applications. For example, cured compositions can be used as a dental sealant or as a matrix material for a composite. Commonly used cured compositions often include polymers having repeating units derived from phenolic compounds, including bisphenols such as bisphenol A (BPA).

SUMMARY OF THE DISCLOSURE

The present disclosure provides a resin having a structure according to at least one of Formula I and Formula II:

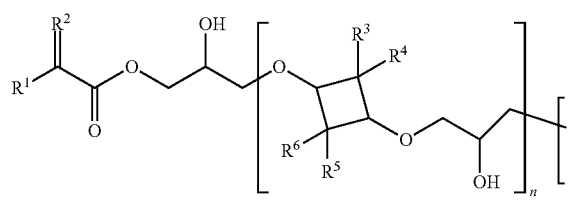
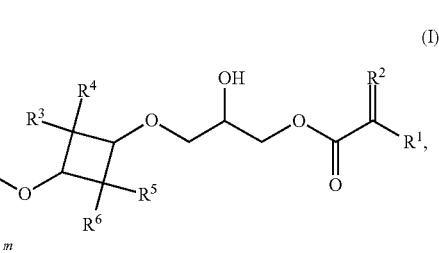

(I)

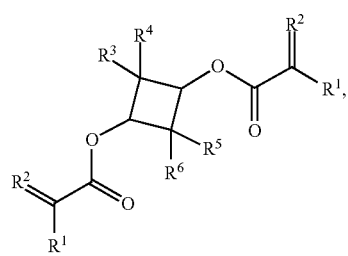

(II)

In Formula I or Formula II $R^1$, $R^3$, $R^4$, $R^5$, and $R^6$ can each be independently selected from the group consisting of hydrogen and substituted or unsubstituted $(C_1\text{-}C_{10})$alkyl. $R^2$ is $(C_1\text{-}C_{10})$alkylene. L is a substituted or unsubstituted $(C_1\text{-}C_{10})$alkylene or $(C_3\text{-}C_{10})$cycloalkylene. In Formula I or Formula II, at least one of n and m is greater than 0, and wherein the resin has an average molecular weight of less than 10,000 g/mol.

The present disclosure further provides a cured product of a curable composition including least one of Formula I and Formula II:

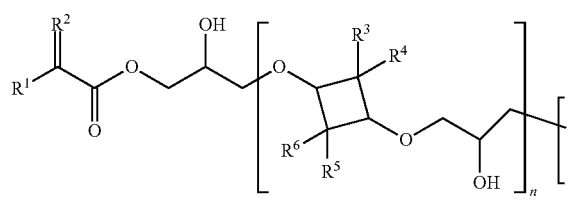
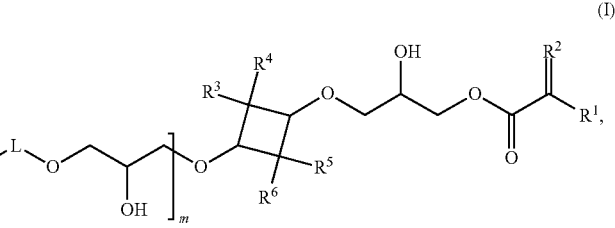

(I)

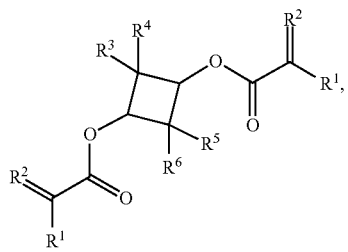

In Formula I or Formula II IV, $R^3$, $R^4$, $R^5$, and $R^6$ can each be independently selected from the group consisting of hydrogen and substituted or unsubstituted $(C_1$-$C_{10})$alkyl. $R^2$ is $(C_1$-$C_{10})$alkylene. L is a substituted or unsubstituted $(C_1$-$C_{10})$alkylene or $(C_3$-$C_{10})$cycloalkylene. In Formula I or Formula II, at least one of n and m is greater than or equal to 0, and wherein the resin has an average molecular weight of less than 10,000 g/mol.

The present disclosure further provides a method of forming a cured product. The method includes curing a curable composition including least one of Formula I and Formula II:

some embodiments, the resins have unexpectedly low viscosities. Additionally, according to some embodiments the resins can be chosen to include no aromatic rings thus enhancing their UV transparency, which can lead to enhances stability on exposure to light and improved cure depth in UV curing systems.

BRIEF DESCRIPTION OF THE FIGURES

The drawings illustrate generally, by way of example, but not by way of limitation, various embodiments discussed in the present document.

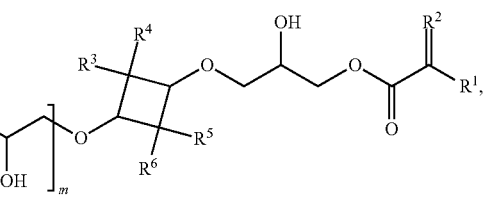

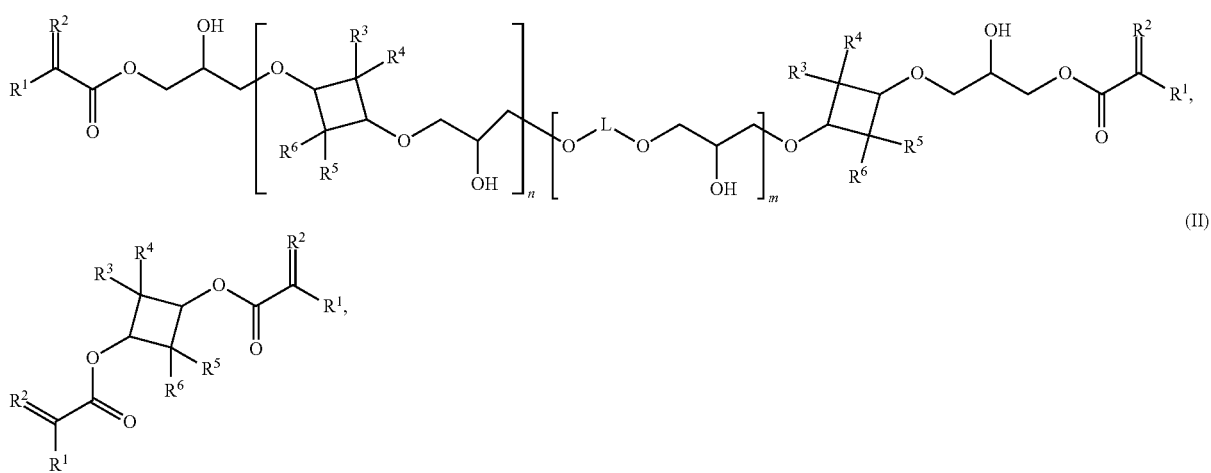

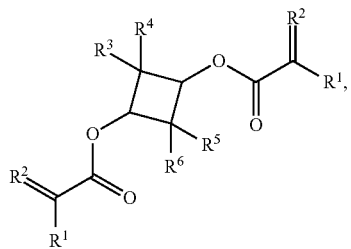

In Formula I or Formula II $R^1$, $R^3$, $R^4$, $R^5$, and $R^6$ can each be independently selected from the group consisting of hydrogen and substituted or unsubstituted $(C_1$-$C_{10})$alkyl. $R^2$ is $(C_1$-$C_{10})$alkylene. L is a substituted or unsubstituted $(C_1$-$C_{10})$alkylene or $(C_3$-$C_{10})$cycloalkylene. In Formula I or Formula II, at least one of n and m is greater than or equal to 0, and wherein the resin has an average molecular weight of less than 10,000 g/mol.

Figure 1:
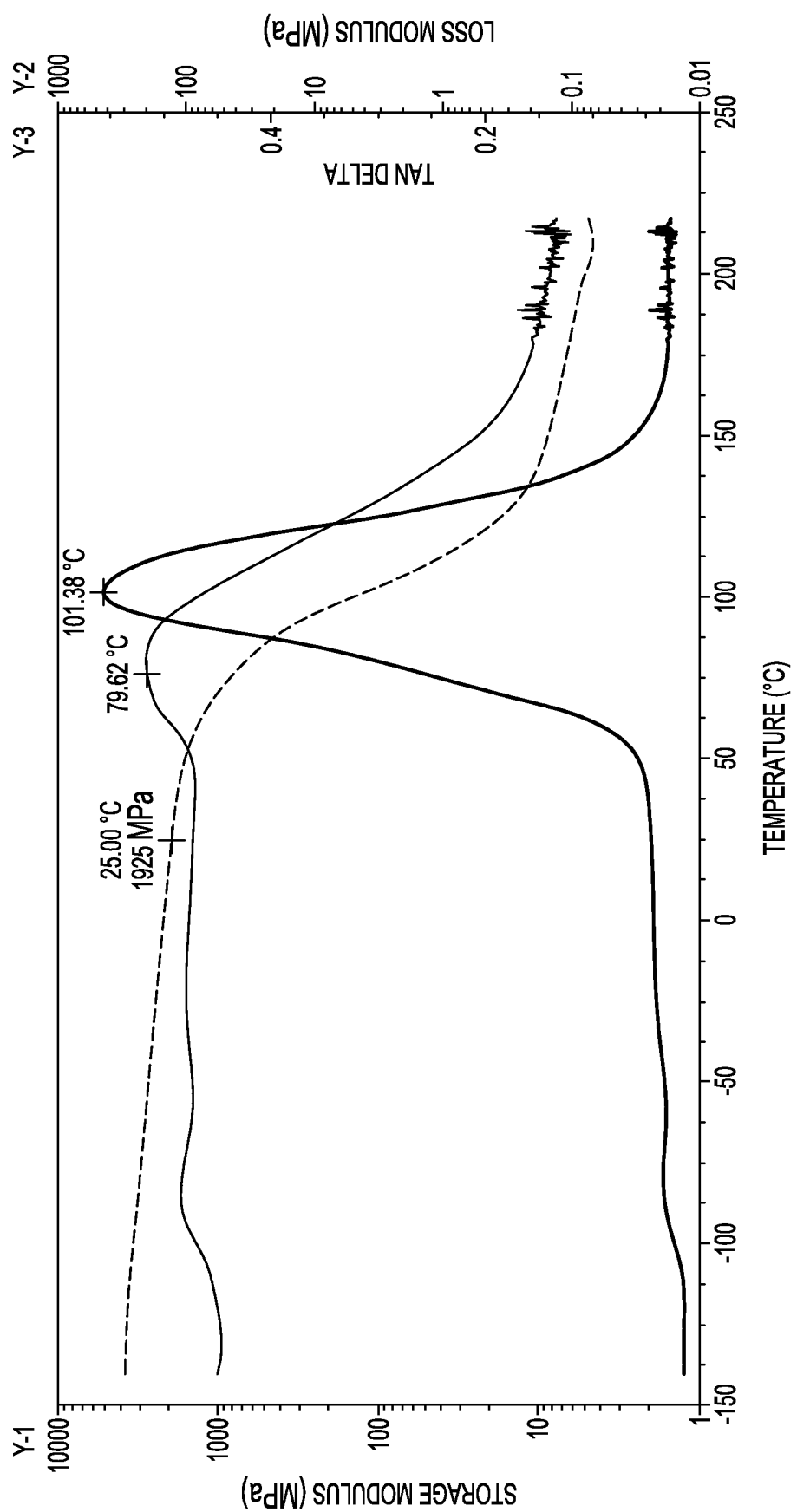

There are several advantages to using the resin or product of the present disclosure, some of which are unexpected. In various embodiments the resin is substantially free of repeating units derived from phenolics. For example, the resin can be substantially free of repeating units derived from bisphenol A (BPA), thus the resin or product has a reduced potential to release endocrine disrupting compounds compared to BPA and other phenolic compounds, whether, for example, due to polymer breakdown or the presence of residual unreacted monomer. Additionally, according to FIG. 1 shows DMA data from a cured bis-GMA-CBDO product of Example 1.

Figure 2:
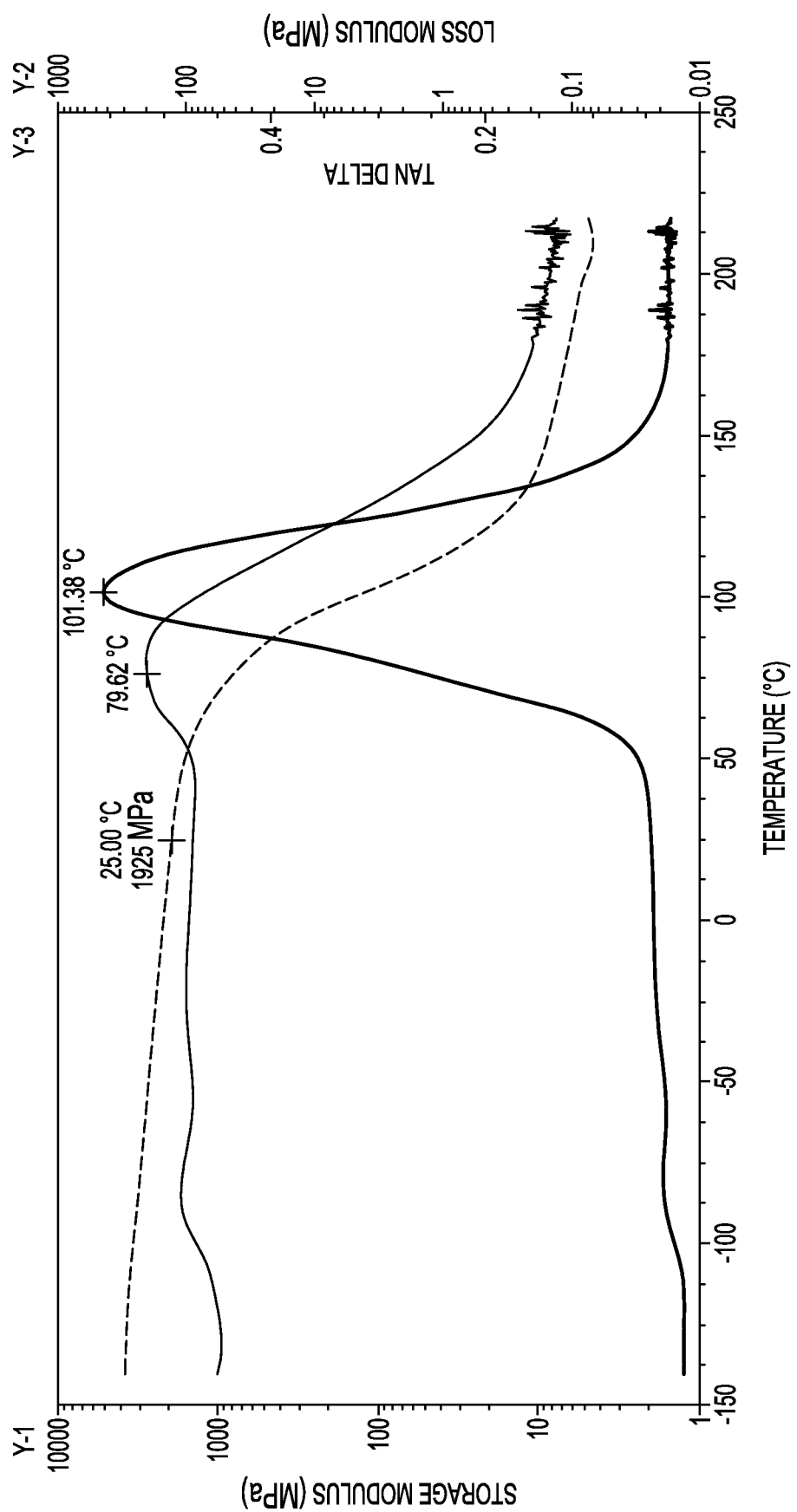

FIG. 2 shows DMA data from a cured bis-GMA-CBDO product of Example 2.

Figure 3:
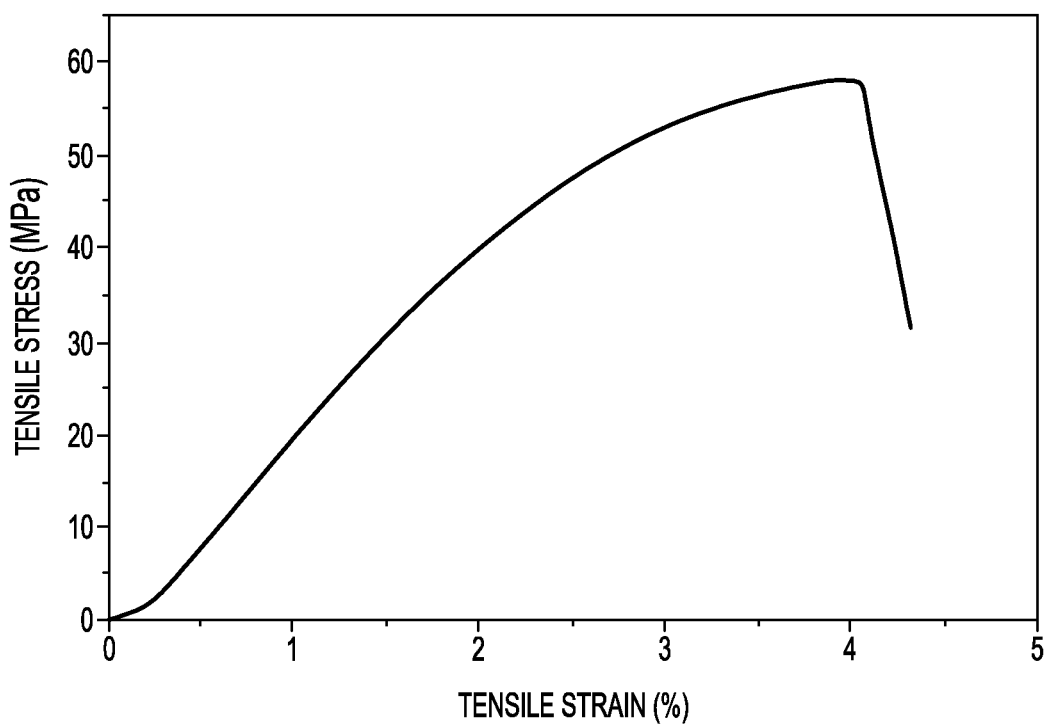

FIG. 3 shows average tensile stress vs. strain curve for cured BIS-GMA-CBDO with 20 wt % styrene of the product of Example 2.

Figure 4:
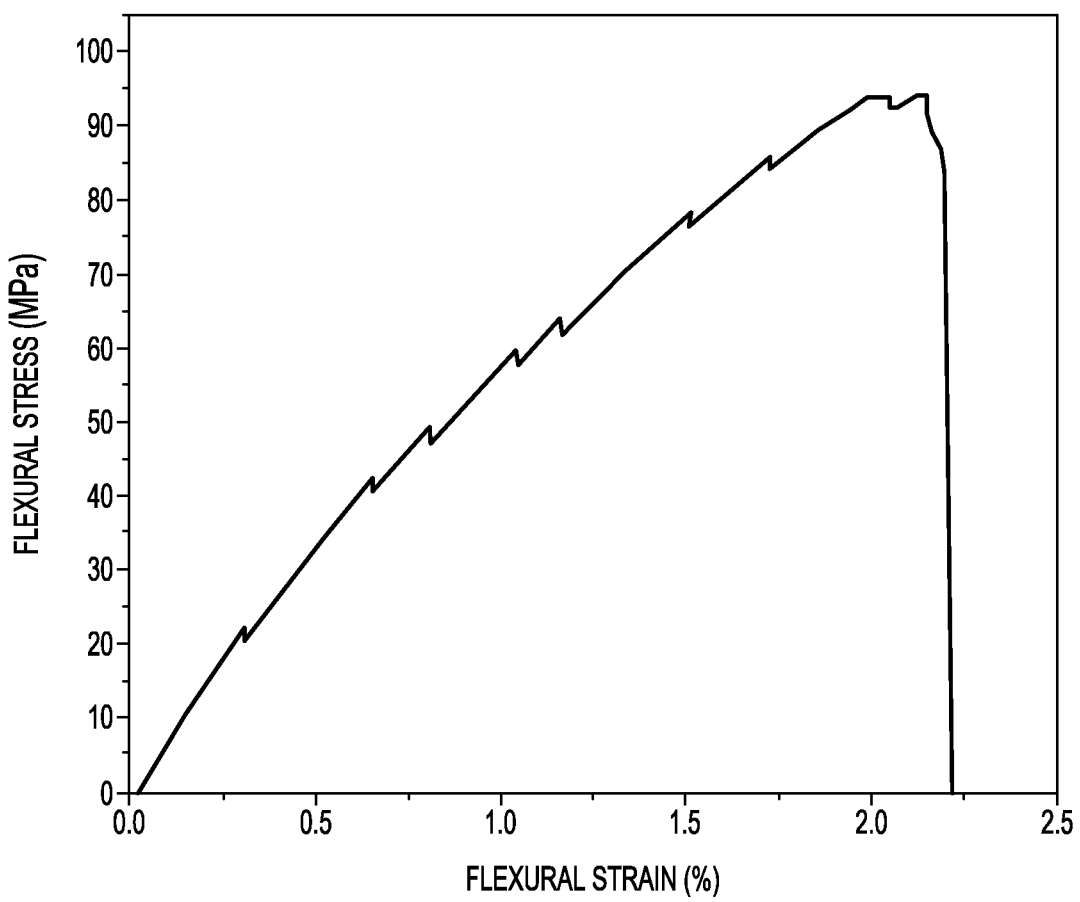

FIG. 4 shows average flexural stress vs. strain curve of the product of Example 2.

DETAILED DESCRIPTION

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the disclosure, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%.

The term "substituted" as used herein in conjunction with a molecule or an organic group as defined herein refers to the state in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein R can be hydrogen or a carbon-based moiety; for example, R can be hydrogen, (C$_1$-C$_{100}$) hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "cycloalkyl" as used herein refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The term "number-average molecular weight" ($M_n$) as used herein refers to the ordinary arithmetic mean of the molecular weight of individual molecules in a sample. It is defined as the total weight of all molecules in a sample divided by the total number of molecules in the sample. Experimentally, $M_n$ is determined by analyzing a sample divided into molecular weight fractions of species i having $n_i$ molecules of molecular weight $M_i$ through the formula $M_n = \Sigma M_i n_i / \Sigma n_i$. The $M_n$ can be measured by a variety of well-known methods including gel permeation chromatography, spectroscopic end group analysis, and osmometry. If unspecified, molecular weights of polymers given herein are number-average molecular weights.

The term "weight-average molecular weight" as used herein refers to $M_w$, which is equal to $\Sigma M_i^2 n_i / \Sigma M_i n_i$, where $n_i$ is the number of molecules of molecular weight $M_i$. In various examples, the weight-average molecular weight can be determined using light scattering, small angle neutron scattering, X-ray scattering, and sedimentation velocity.

In the area of dental sealants and composites, a material known as bis-GMA, bis(glycidyl methacrylate) of bisphenol A, provides good cure response, low shrinkage, and a wide range of useful and appropriate mechanical characteristics for the aforementioned applications. However, it suffers from two major drawbacks. First, it is a highly viscous material, requiring reactive diluents in order to make its use practical. Second, it is based on bisphenol A, a material now widely recognized for its endocrine disrupting potential and is under scrutiny in any application with a potential for human exposure—a point of increasing concern among dental professionals. While interest in alternatives is growing, in its BPA Free Dental Materials Guide, the Eco Dentistry Association lists only two dental resin suppliers (both producing dental composites only, not sealants) who specifically identify their products as BPA-free.

Additionally, vinyl ester (VE) resins like bis-GMA as well as related unsaturated polyester (UP) resins find use as matrix materials in all manner of fiber composites and industrial coatings, where they can provide low viscosity and good performance at lower cost than competing epoxy resins. As in the case of dental applications, the use of reactive diluents can be necessary for the realization of acceptable viscosity levels, especially in composite applications where resin infusion into glass and carbon fiber fabrics is important. An effective means of realizing the desired viscosity and performance levels at a reasonable price point involves the use of significant amounts of styrene (about 35-50%) as a reactive diluent. While these applications do not generate the same levels of concern over bisphenol A exposure to the end user, the use of large quantities of styrene is a major issue, as it is a volatile organic compound (VOC), a hazardous air pollutant (HAP), and, as such, a serious inhalation hazard for anyone handling these resins and a source of odor and outgassing even after curing.

This disclosure relates to the creation of unsaturated mono- or difunctional resin monomers that can be based on 2,2,4,4-tetramethyl-1,3-cyclobutanediol, or CBDO. These resins, differ from various resins previously used, (e.g., in dental applications), which are based on bis-GMA or other bisphenol A derivatives. The resins can be included in a curable composition that can be cured to form a cured composition. The cured composition can be used in many different applications. Examples of suitable applications include as a dental sealant material or as a matrix material for a composite (e.g., a dental composite, a fiber composite, etc.).

According to some embodiments of the present disclosure, a cured composition can be formed from a curable composition including one or more epoxy vinyl ester resins or vinyl ester resins. The one or more resins having structure according to at least one of Formula I and Formula II:

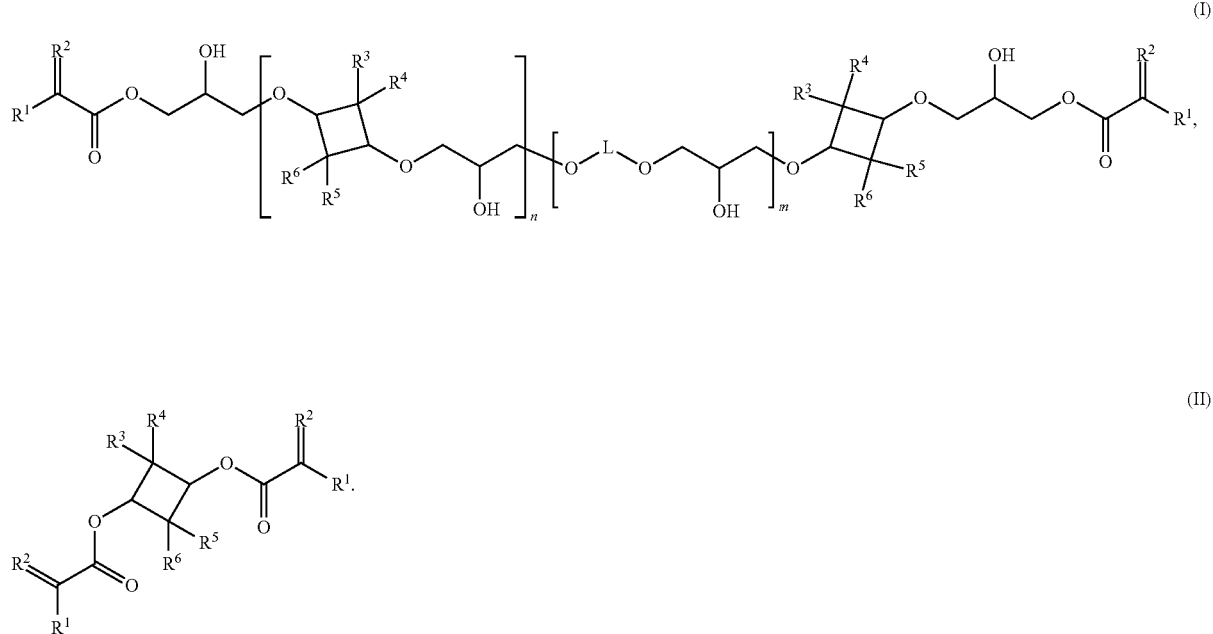

In Formula I or Formula II $R^1$, $R^3$, $R^4$, $R^5$, and $R^6$ can each be independently selected from the group consisting of hydrogen and substituted or unsubstituted $(C_1-C_{10})$alkyl. $R^2$ is $(C_1-C_{10})$alkylene. L is a substituted or unsubstituted $(C_1-C_{10})$alkylene (e.g., a di-substituted alkly radical) or $(C_3-C_{10})$cycloalkylene (e.g., a di-substituted cycloalkly radical). In either Formula I or Formula II, at least one of n and m is greater than or equal to 0, and the resin has an average molecular weight of less than 256 g/mol to about 10,000 g/mol or from about 2,000 g/mol to about 7,000 g/mol. In some embodiments, n can range from 0 up to 2, 5, 10, 15 or 20. In some embodiments n+m can range from to 0 to 30. In some embodiments, the resin of Formula I is a bis-GMA-CBDO resin with m=0, represented as:

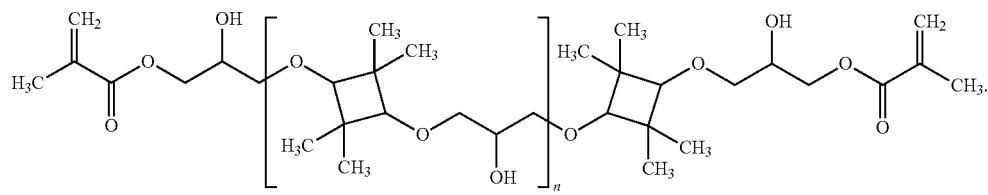

In some embodiments, the resin of Formula II is a CBDO dimethacrylate represented as:

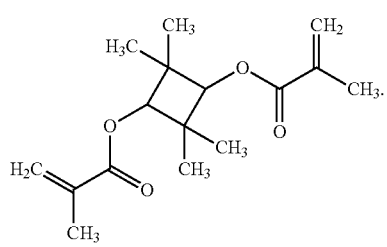 [SMILES: C=C(C)C(=O)OC1C(C)(C)C(OC(=O)C(=C)C)C1(C)C]

The resin according to Formulas I and II can have many suitable physical properties. For example, a density at room temperature can be in a range of from about 1 g/ml to about 2 g/ml, about 1.05 g/ml to about 1.10 g/ml, or less than, equal to, or greater than about 1 g/ml, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95, or 2.00. Additionally, a viscosity of the resins can be in a range of from about 1,500 mPa s to about 6,500 mPa s, about 2,000 mPa s to about 5,000 mPa s, or less than, equal to, or greater than about 1,500 mPa s, 2,000, 2,500, 3,000, 3,500, 4,000, 4,500, or about 5,000 mPa s.

According to some embodiments, a method of making the resin of Formula I includes reacting a resin according to the structure of Formula III, which can be a diglycidyl ether of CBDO, with a monomer according to Formula IV. The structure of Formula III is represented below:

Formula IV is an unsaturated carboxylic acid. The structure of Formula IV is represented below:

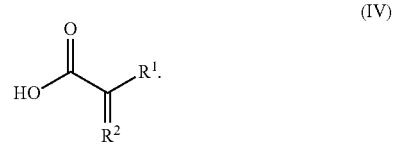

(IV)

In some embodiments the structure of Formula III is methacrylic acid as shown below:

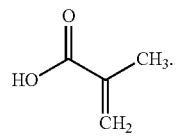

According to some embodiments, a method of making the resin of Formula III includes reacting a molecule according to Formula V with a molecule according to Formula VI. The structure of Formula V is represented below:

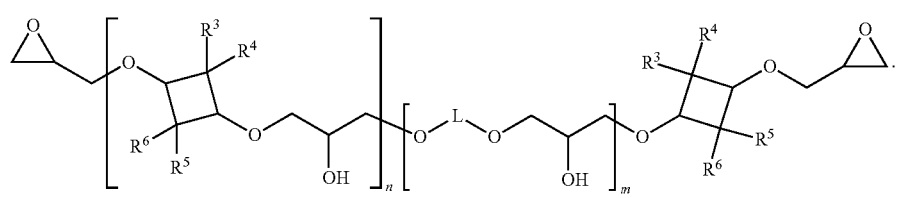

(III)

In some embodiments, the structure of Formula III where m=0 can be represented as:

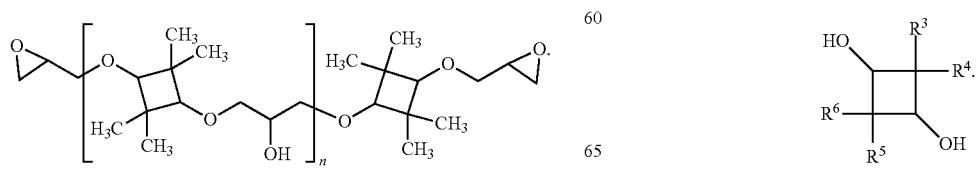

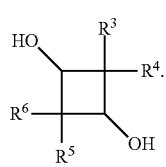

V

In some embodiments, the structure of Formula V is 2,2,4,4,-tetramethyl-1,3-cyclobutanediol as shown below:

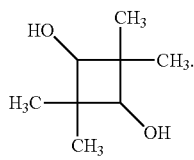

Formula VI is an epoxide. The structure of Formula VI is represented below:

In Formula VI, X is selected from the group consisting of OH, F, Cl, Br, and I.

In some examples, the structure of Formula VI is epichlorohydrin as shown below:

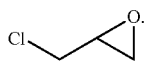

As described herein, a cured product of a curable composition including at least one of the structures according to Formula I and Formula II can be formed. In the curable composition at least one of the structures according to Formula I and Formula II ranges from about 1 wt % to about 100 wt % of the cured product, or about 5 wt % to about 95 wt %, about 40 wt % to about 90 wt %, about 60 wt % to about 80 wt %, about 10 wt % to about 20 wt %, less than, equal to, or greater than about 35 wt %, 40, 45, 50, 55, 60, 65, 70, 75, 80, 85, 90, 95, or 100 wt %.

In addition to either the structure of Formula I, Formula II, or a mixture thereof the composition can include components such as an initiator component. In some examples the initiator component can be a radical initiator. In some examples the radical initiator component can be a photoinitiator or photoinitiator system. The initiator can be in a range from about 0.1 wt % to about 25 wt % of the composition, about 1 wt % to about 10 wt %, about 5 wt % to about 7 wt %, less than about, equal to about, or greater than about 0.1 wt %, 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, or 25 wt %.

Suitable examples of initiators include methyl ethyl ketone peroxide, 2,4,6-trimethylbenzoyldiphenylphosphine oxide, camphorquinone, benzoyl peroxide, phthaloyl peroxide, naphthoyl peroxide, alkyl- or alkanoyl-substituted peroxides such as acetyl, caproyl, lauroyl, tertiary butyl and di-t-butyl peroxides, alkyl-, alkanoyl- or chloro-substituted benzoyl peroxides such as acetyl benzoyl peroxide, dimethyl benzoyl peroxide and 2,4-dichloro-benzoyl peroxide, hydroperoxides such as di-isopropyl-benzene hydroperoxide, t-butyl hydroperoxide, and cumene hydroperoxide, cinnamoyl peroxide, methyl ethyl ketone peroxide, 1-hydroxy-cyclohexyl-phenylketone, 2,2-dimethoxy-2-phenylacetophenone, urea peroxide, or mixtures thereof. In other examples the initiator component can be an anionic initiator. Suitable anionic polymerization initiators include alkali metal alkoxides, such as potassium, sodium or lithium methoxide, ethoxide, propoxide, isopropoxide, butoxide, or mixtures thereof.

The composition can further include a reactive diluent. The reactive diluent can be in a range of about 0.01 wt % to about 70 wt % of the composition, about 5 wt % to about 60 wt %, about 20 wt % to about 50 wt %, less than about, equal to about, or greater than about 0.01 wt %, 0.5, 1, 5, 10, 15, 20, 25, 30, 35, 40, 45, 50, 55, 60, 65, or 70 wt %. Suitable examples of reactive diluents include styrene, triethylene glycol dimethacrylate, methyl methacrylate, butyl acrylate, butyl methacrylate, alpha methyl styrene, vinyl toluene, para-methyl styrene, diallyl phthalate, diallyl isophthalate, octyl acrylamide, trimethylol propane triacrylate, triallyl cyanurate, triallyl isocyanurate, diallyl malenate, diallyl tetrabromophtalate, ethyl methacrylate, n-propyl methacrylate, iso-propyl methacrylate, n-butyl methacrylate, iso-butyl methacrylate, sec-butyl methacrylate, tert-butyl methacrylate, the amyl methacrylates, ethylene dimethacrylate, butylene dimethacrylate, ethylene glycol monomethacrylate, ethylene glycol dimethacrylate, diethylene glycol dimethacrylate, triethylene glycol dimethacrylate, tetraethylene glycol dimethacrylate and mixtures thereof. Compositions including these diluents can be stable (e.g., free of gelation or precipitation) when stored at room temperature, under dark conditions, for any suitable amount of time, for example greater than or equal to 1 month, greater than or equal to 2 months, greater than or equal to 3 months, greater than or equal to 4 months, greater than or equal to 5 months, greater than or equal to 6 months, greater than or equal to 7 months, greater than or equal to 8 months, greater than or equal to 9 months, greater than or equal to 10 months, greater than or equal to 11 months, or greater than or equal to 12 months.

In some examples, the composition can further include an accelerator. The accelerator can range from about 0.001 wt % to about 10 wt % of the composition, about 0.5 wt % to about 4 wt %, about 1 wt % to about 3 wt %, less than, equal to, or greater than 0.001 wt %, 0.5, 1, 1.5, 2, 2.5, 3, 3.5, 4, 4.5, 5, 5.5, 6, 6.5, 7, 7.5, 8, 8.5, 9, 9.5, or 10 wt %. Examples of suitable accelerators include cobalt naphthenate N,N-dimethylaniline, N, N-diethylaniline, 1,4-diazabicyclo[2.2.2]octane, 1,8-diazabicyclo[5.4.0]undec-7-ene, 1,5-diazabicyclo[4.3.0]non-5-ene, di-n-propylamine, n-hexylamine, or mixtures thereof.

In some examples, the composition can include an inhibitor. The inhibitor can range from about 0.0001 wt % to about 10 wt % of the composition, about 0.01 wt % to about 4 wt %, about 1 wt % to about 3 wt %, less than, equal to, or greater than 0.0001 wt %, 0.01, 1, 1.5, 2, 2.5, 3, 3.5, 4, 4.5, 5, 5.5, 6, 6.5, 7, 7.5, 8, 8.5, 9, 9.5, or 10 wt %. Examples of suitable inhibitors include 2,4-pentanedione, t-butyl catechol, butylated hydroxyl anisole (BHA), butylated hydroxytoluene (BHT), hydroquinone, or a methyl ether of hydroquinone (MEHQ).

To form the cured product the curable composition is cured. The composition can be cured through many suitable techniques. For example, the composition can be exposed to visible radiation, UV radiation, electron beam radiation or gamma ray radiation. The source of ultraviolet radiation, visible radiation, electron beam radiation or gamma ray radiation can be any suitable source. Examples of suitable sources include an Hg lamp or a light emitting diode (LED). For gamma rays a suitable source is $^{60}$Co. Additionally, the curable composition can be cured at room temperature or elevated temperature (e.g., up to 150° C.) followed by a post-cure bake. During the post-cure bake, the cured composition can be increased to a temperature of about 50° C. to about 200° C., about 100° C. to about 140° C., about 110° C. to about 130° C., less than, equal to, or greater than 50°

C., 55, 60, 65, 70, 75, 80, 85, 90, 95, 100, 105, 110, 115, 120, 125, 130, 135, 140, 145, 150, 155, 160, 165, 170, 175, 180, 185, 190, 195 or 200° C. More generally, the cured composition can be post-cure baked at a temperature above the final $T_g$ but below the decomposition temperature of the cured composition.

The curable composition can be deposited to any number of surfaces or objects. For example, the composition can be deposited on a tooth and cured thereon to form a sealant, or combined with appropriate particulate fillers, applied to fill defects in a tooth, then cured in place to create a composite filling. In other examples, fabrics or textiles comprised of reinforcing fibers such as polymeric, carbon and/or glass fibers can be infused with the composition, then cured to form a composite material. Additionally, the curable composition can be deposited on a substrate and cured thereon to form a coating.

EXAMPLES

Various embodiments of the present disclosure can be better understood by reference to the following Examples which are offered by way of illustration. The present disclosure is not limited to the Examples given herein.

Example 1: Small Scale Synthesis of Bis-GMA-CBDO Resin, Cross Linking and Characterization Thereof A diglycidyl ether of CBDO (CBDO-DGE) was reacted with methacrylic acid in the presence of triphenylphosphine as a catalyst and with hydroquinone added as an inhibitor to prevent free radical polymerization of the carbon-carbon double bonds present in the system.

In a single necked round bottom flask CBDO diglycidyl ether (CBDO-DGE) (10 g, 39 mmol), methacrylic acid (6.71 g, 78 mmol), triphenylphosphine (100 mg, 0.38 mmol) and hydroquinone (100 mg, 0.90 mmol) were introduced. The flask was connected to a reflux condenser and the reaction mixture was vigorously stirred at 120° C. After 6 h the reaction was stopped by cooling to room temperature. A quantitative yield of bis-GMA-CBDO was obtained, with the product stored in the dark to avoid any spontaneous reaction of the unsaturated bonds it contained. The structure of the obtained bis-GMA-CBDO was determined via $^1$H-NMR in CDCl$_3$ with the chemical shifts for the vinyl, the adjacent methyl, and the CBDO methyl moieties indicated; their integrations correspond to the targeted bis-GMA-CBDO structure, providing further proof of a successful synthesis.

The obtained bis-GMA-CBDO was mixed with 40 wt % styrene as a reactive diluent. Methyl ethyl ketone peroxide (1.5 wt %) was then added as a free radical initiator and the combination mixed thoroughly. Cobalt naphthenate (0.2 wt %) was then added as an accelerator and the combination again mixed thoroughly. This mixture was then allowed to cure at room temperature for 16 hours followed by a post-cure bake at 110° C. for 3 hours to yield a stiff, tack-free solid product.

Dynamic mechanical analysis was performed on the cured bis-GMA-CBDO based network to yield storage modulus, loss modulus, and tan δ as a function of temperature (FIG. 1). The results of this analysis indicate that the crosslinked material possesses a modulus of about 1.9 GPa at room temperature and a glass transition temperature of about 80° C. (as derived from the peak in the DMA loss modulus curve associated with the main relaxation). For comparison purposes, a typical vinyl ester resin based on the BPA-derived bis-GMA and containing a similar concentration of styrene monomer provides a modulus of about 3.2 GPa at room temperature and a glass transition temperature of about 120° C. (as derived in the same fashion as above) when cured in an analogous fashion as well as a viscosity of around 700,000 mPa·s.

Example 2: Large Scale Synthesis of Bis-GMA-CBDO Resin, Cross Linking and Characterization Thereof The large scale synthesis of BPA free bis-GMA-CBDO was performed according to the following protocol. In a single necked round bottom flask CBDO-DGE (100 g, 390 mmol), methacrylic acid (67.1 g, 780 mmol), triphenylphosphine (1 g, 3.8 mmol) and hydroquinone (1 g, 9 mmol) were introduced. The flask was connected to a reflux condenser and the reaction mixture was vigorously stirred at 120° C. After 6 h the reaction was stopped by cooling to room temperature. The resulting bis-GMA-CBDO was a viscous yellow liquid. To prevent any unwanted formation of free radicals which would then initiate crosslinking, the obtained bis-GMA-CBDO was stored under nitrogen in the dark. A quantitative yield of bis-GMA-CBDO was obtained. Triphenylphosphine and hydroquinone, which are cheap commercially available chemicals, were used in the reaction as the catalyst and inhibitor respectively. The reaction was also performed on a smaller scale initially without the presence of hydroquinone. However, in the absence of the hydroquinone inhibitor, the viscosity of the reaction mixture was observed to increase with time and at the end of 6 hours an intractable solid product was obtained. This can be attributed to the generation of thermally induced free radicals which caused gelation of the reaction mixture. For the reaction mixture that contained the inhibitor the obtained yellow viscous liquid was soluble in all common organic solvents. In order to evaluate the structure of the obtained product, $^1$H NMR spectroscopy was performed. To remove the catalyst and the inhibitor, 5 g of the obtained product was dissolved in 5 mL of chloroform and washed with 5 mL of deionized water. The aqueous phase was then decanted the procedure repeated 3 times. The chloroform solution of bis-GMA-CBDO was then twice dried over anhydrous sodium sulfate to remove any remaining aqueous phase. The chloroform was then removed under vacuum at room temperature and the isolated bis-GMA-CBDO was dissolved in deuterated chloroform for the NMR characterization.

The $^1$H NMR spectrum showed peaks for the vinyl protons, which were observed around 5.6 and 6.1 ppm. The peaks for the methyl groups adjacent to the vinyl moieties were observed at 1.8 ppm, and the methyl groups from CBDO were observed around 1.0 ppm. The integrations of the peaks are consistent with the number of protons expected in the structure, thus confirming the synthesis of CBDO-VER. Using a volumetric flask, the density of the obtained bis-GMA-CBDO was determined to be about 1.08 g/ml at room temperature.

The synthesized bis-GMA-CBDO was mixed with 20 wt % styrene as the reactive diluent. This mixture was stored at room temperature in a dark location, and was stable under these conditions for over 6 months, with no gelation or precipitation. To obtain cured bis-GMA-CBDO samples, concentrations of 1.25 phr, 1.5 phr, and 2.0 phr of methyl ethyl ketone peroxide (MEKP, Norox MEKP-925H) were used as the initiating species and 0.1 phr, 0.2 phr, and 0.4 phr of cobalt naphthenate (CoNap, 6% in mineral spirits, Sigma Aldrich) were used as the accelerator. In an example formulation step, the MEKP was first added to the bis-GMA-CBDO solution in styrene and mixed at 1000 rpm for 1 min using a FlackTek 600.1 VAC-P Speedmixer. The accelerator was then introduced to the formulation, which was then mixed at 1000 rpm for 1 min using the same mixing procedures. The resulting mixture was then cured at 25° C. and the time required for tack-free cure was monitored, followed by post-curing at 120° C. for two hours to ensure full cure. By measuring the weight of a known volume (5 mL), the density of the uncured bis-GMA-CBDO formulation containing 20 wt % styrene was measured to be 1.04 g/mL at room temperature. In contrast, the density of the fully cured sample was measured (using ASTM D792) and found to be 1.1 g/mL. For bis-GMA-CBDO with 20 wt % styrene, this implies volume shrinkage of 5.4% on curing. For comparison purposes, a conventional vinyl ester resin (VER) prepared from the equivalent BPA-based epoxy resin and combined with 20 wt % styrene has been reported to experience a volume shrinkage of about 13% on curing.

Curing characteristics for bis-GMA-CBDO with 20 wt % styrene are summarized in Table 1. Fully cured samples from commercially available Derakane 411-400 resin were also prepared for hardness testing with similar procedure used from the bis-GMA-CBDO resin.

TABLE 1

Curing characteristics of bis-GMA-CBDO formulations with 20 wt % styrene

| Time to Full Cure (h) | MEKP (phr) | CoNap (Phr) | Volume Shrinkage (%) |
|---|---|---|---|
| 30 | 1.25 | 0.1 | — |
| 22 | 1.5 | 0.2 | 5.4 |
| 12 | 2.0 | 0.4 | — |

To characterize the thermomechanical properties of bis-GMS-CBDO, a plaque of cured bis-GMA-CBDO was produced. The formulation containing 1.5 phr MEKP and 0.2 phr CoNap, which is the formulation most representative of conventional VER systems, was cast in an aluminum mold and cured at 25° C. for 24 hours followed by post curing at 120° C. for 2 hours. The curing procedure yielded a stiff, non-tacky cured bis-GMA-CBDO plaque. The plaque was then cut and the surface polished to obtain specimens for further characterization.

Dynamic mechanical rheological testing was performed on cured bis-GMA-CBDO specimens using a TA Instruments Q800 dynamic mechanical analyzer (DMA). Testing was performed in dual cantilever beam mode from −150° C. to 220° C. at a heating rate of 10° C./min in order to assess the temperature-dependent viscoelastic behavior and alpha transition temperature of the materials. A maximum displacement of 25 μm and a frequency of 1 Hz were utilized. Representative storage modulus (E'), loss modulus (E"), and tan δ data obtained via the DMA analysis of cured bis-GMA-CBDO with 20 wt % styrene is displayed in FIG. 2. As shown the data in the DMA plot of FIG. 1 is substantially similar to that of FIG. 2 thus showing consistent behaviors between large and small scale synthesized products. The alpha transition temperature ($T_\alpha$) of cured bis-GMA-CBDO specimens was determined to be about 80° C. based on the E" curve and about 100° C. based on the tan δ curve, and a room temperature storage modulus of about 1.9 GPa was observed. A β-relaxation was also observed around −90° C. In comparison, a conventional vinyl ester containing 20 wt % styrene was reported to give a (compressive) elastic modulus of 3 GPa and a glass transition temperature of 150° C., the latter based on both DMA tan δ and DSC data.

Barcol Hardness measurements were performed on cured bis-GMA-CBDO specimens according to ASTM D-2583 using a Bareiss HPE II Digital Durometer. Samples were placed under the indenter of the durometer and a uniform pressure was applied until the dial indentation reached a maximum. 10 individual readings were taken on 3 samples and the average of all the readings was calculated. Based on these results, a Barcol hardness of 30±1 was observed for the cured bis-GMA-CBDO samples at room temperature. In comparison, for a conventional BPA-based vinyl ester a Barcol hardness of 35±2 has been reported.

Tensile testing on the cured bis-GMA-CBDO specimens was performed according to ASTM D638. The tensile test was performed with a preload of 10 N and a crosshead displacement rate of 5 mm/min on an Instron load frame (Model 6025). A strain gauge extensometer was used to accurately measure the displacement, from which the strain was calculated. Five specimens were tested, with average dimensions of 125 mm×14.2 mm×1.6 mm (L×W×T). The average stress vs. strain curve for the specimens is displayed in FIG. 3, which is a graph showing average tensile stress vs. strain curve for cured BIS-GMA-CBDO with 20 wt % styrene. Using the obtained tensile data, the mechanical properties were determined. The results are summarized in Table 2. For comparison the reported mechanical properties of an analogous BPA-based VER are shown in brackets in Table 2.

TABLE 2

Tensile properties of cured bis-GMA-CBDO with 20 wt % styrene (and a conventional VER control, also with 20 wt % styrene)

| Young's Modulus (GPa) | Maximum Tensile Stress (MPa) | Strain at Break (%) | Tensile Stress at Break (MPa) |
|---|---|---|---|
| 2.2 (1.8) | 57 (44) | 4 (2.4) | 57 (44) |

Glass fiber reinforced composites of the bis-GMA-CBDO formulations were processed using a vacuum assisted resin transfer molding (VARTM) process. In this process unidirectional E glass fabrics (Saertex 955, Fibre Glast) were used as the reinforcement. The formulation of bis-GMA-CBDO with the initiator and promoter was prepared as described above. This mixture was then infused in the unidirectional glass fabrics under vacuum on a planar glass substrate, after which curing was cured out at 25° C. for 24 hours followed by post-curing at 120° C. for two hours. The obtained composite was a stiff, opaque plaque with no observable voids and was light brown in color. Specimens were then cut from the plaque and their edges were polished prior to the characterization. Using ASTM D3171, constituent component analysis of the composite was performed. The specimens were placed in ceramic crucibles and weighed. They were then placed in a muffle furnace (Thermolyne Corporation FC2025P) at 565° C. to thermally degrade the cured bis-GMA-CBDO matrix. The samples were kept in the furnace such that only the glass reinforcement remained and all the char was removed. The crucibles were then cooled down to room temperature, weighed again and the constituent component analysis was performed using the known densities of the glass fiber reinforced composite, the glass fiber, and the resin, which allowed for the calculation of the volume fraction of glass, matrix material and voids. The results of the analysis are summarized in Table 3.

TABLE 3

Constituent component analysis of cured unidirectional glass fiber bis-GMA-CBDO composites

| Glass Fraction (vol %/wt %) | Matrix Fraction (vol %/wt %) | Void Fraction (vol %) |
|---|---|---|
| 50 ± 3/71 ± 2 | 46 ± 2/28 ± 2 | 3.3 ± 0.7 |

Flexural properties were characterized for the bis-GMA-CBDO unidirectional glass fiber composite specimens using the ASTM D7264 3-point bend testing. The specimens were cut in the axial direction such that the glass fiber orientation was along the length of the specimen. The specimens were milled such that the width was 12.7 mm. The support span used was varied as a function of sample thickness and determined by a support span-to-thickness ratio of 20:1. An Instron 4481 load frame with a ±5 kN load cell was used for the testing, which was carried out at a loading rate of 1.0 mm/min. The average flexural stress vs. strain curve is displayed in FIG. 4. The results of the flexural testing are summarized in Table 4, which show mechanical (flexural) properties of a cured bis-GMA-CBDO unidirectional glass fiber composite containing 20 wt % styrene and reinforced with about 51 vol %/72 wt % unidirectional E glass (and a conventional VER containing 45 wt % styrene and reinforced with about 41 vol %/about 60 wt % unidirectional E glass).

TABLE 4

Flexural properties of cured bis-GMA-CBDO.

| Flexural Modulus (GPa) | Maximum Flexural Stress (MPa) | Flexural Strain at Break (%) |
|---|---|---|
| 7.5 ± 0.5 (8.3) | 97 ± 11 (79.2) | 2 ± 0.3 (—) |

The flexural properties measured for the bis-GMA-CBDO/glass fiber composite specimen is competitive with what has been measured in the case of flexural testing of a conventional VER containing 45 wt % styrene and reinforced with about 41 vol %/about 60 wt % unidirectional glass fiber. While the higher modulus in the conventional system is at least partially explained by the higher modulus of the conventional base resins, the higher strength of the bis-GMA-CBDO implies that good interfacial stress transfer is taking place.

There are several non-limiting reasons to use the resins or products described herein. First, according to some embodiments, the structure of the bis-GMA-CBDO resins are substantially free of structures derived from bisphenol A as well as from phenolic compounds more broadly, addressing the health and safety concerns associated with this class of molecules and their tendency to act as endocrine disruptors. Second, according to some embodiments, it was found that CBDO-DGE, even in the impure form (i.e. with oligomers present), possessed an unexpectedly low viscosity of about 37 mPa·s, far lower than some corresponding BPA-based epoxies (4,000-14,000 mPa.$). In view of the viscosities for BPA-based epoxy resins and bis-GMA imply, an increase in viscosity of about 50-175× can be expected when reacting methacrylic acid with an epoxy resin to produce the corresponding dimethacrylate. By analogy, then, the bis-GMA-CBDO resins would be expected to have any suitable viscosity. For example, the viscosity can be in the range of about 1,500-6,500 mPa·s. This is so much lower than the viscosity of the bis-GMA that it could enable a wide range of formulating possibilities that are currently out of the question. In the context of both dental resins and vinyl ester/unsaturated polyester resins, the use of reactive diluents could be massively reduced if not entirely eliminated, simplifying formulating in the former case and addressing styrene emissions in the latter case. In the case of dental composites, lower viscosities and greater flowability imply better penetration of sealants and composite materials into fissures, defects, etc. and enhanced adhesion and durability as a result. A lower viscosity base resin would allow the use of higher levels of fillers and nanofillers, thus enabling the preparation of dental composites with higher mechanical performance than current resin systems allow. Along the same lines, lower viscosities in the context of fiber composite applications would simplify composite formation, allowing for more rapid resin even without a strong vacuum source, reducing the probability of entrapped voids in composite parts and enhancing performance there as well. Further variations on this theme could be achieved by using a copolymeric high molecular weight CBDO-based epoxy as the basis for additional vinyl ester resins.

All of the aforementioned arguments hold for the CBDO-DMA material as well; in fact, CBDO-DMA is expected to possess an even lower viscosity than bis-GMA-CBDO, given its lower molecular weight and lack of hydroxyl groups (hydrogen bonding promotes viscosity increases). In particular, the viscosity of CBDO-DMA could be similar to that of CBDO-DGE (about 37 mPa.$). In addition to having potential as an ultra-low viscosity, high performance base resin, CBDO-DMA could also serve as a high-performance reactive diluent in vinyl ester and unsaturated polyester resins, addressing issues associated with styrene content in the latter.

Additional reactions to produce low molecular weight CBDO-based monomers with unsaturated carbon-carbon bonds are possible as well. As implied by the above discussions, it is possible to react acrylic acid with CBDO-DGE to produce the bis(glycidyl acrylate) of CBDO, or bis-GA-CBDO. By the same token, direct reaction of CBDO with acrylic acid is also possible, and could yield CBDO diacrylate (CBDO-DA). Divinyl ether and diallyl ether derivatives of CBDO may also be envisioned. All of these materials could provide an attractive combination of low viscosity and high performance.

Finally, another advantage of these CBDO-based materials as a class, according to some embodiments, is that they contain no aromatic rings, thus enhancing their UV transparency. This is especially relevant in the context of monomers containing unsaturated carbon-carbon bonds, as UV and visible light curing are commonly used in combination with appropriate photoinitiators in order to induce polymerization. This enhanced transparency could allow for better penetration of the light, the curing of thicker sections of material, and the realization of a more rapid, more complete cure in less time. In dental applications in particular, this would help to address potential health issues caused by the leaching of unreacted species, while in fiber composites and industrial coating applications, this would ensure maximum durability.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present disclosure. Thus, it should be understood that although the present disclosure has been specifically disclosed by specific embodiments and optional features, modification and variation of the concepts herein disclosed may be resorted to by those of ordinary skill in the art, and that such modifications and variations are considered to be within the scope of embodiments of the present disclosure.

ADDITIONAL EMBODIMENTS

The following exemplary embodiments are provided, the numbering of which is not to be construed as designating levels of importance:

Embodiment 1 provides a resin having a structure according to at least one of Formula I and Formula II.

Embodiment 3 provides the resin of any one of Embodiments 1-2 wherein the resin of Formula II is:

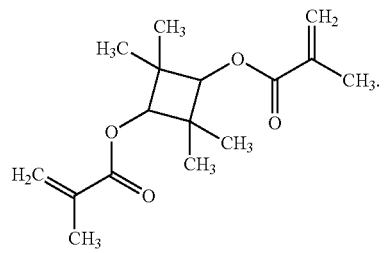

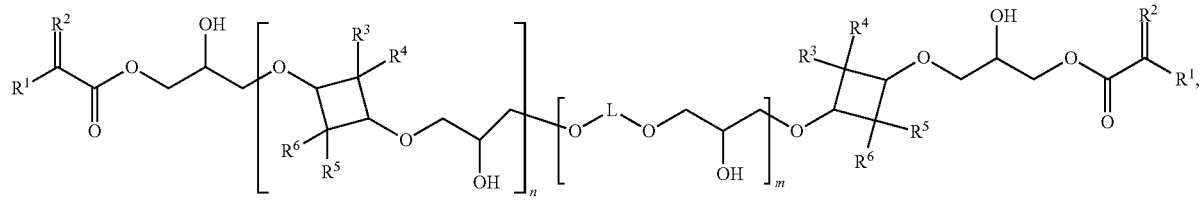

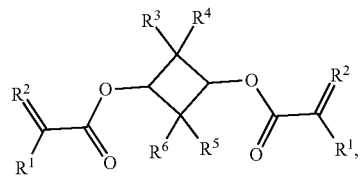

wherein
R$^1$, R$^3$, R$^4$, R$^5$, and R$^6$ are each independently selected from the group consisting of hydrogen and substituted or unsubstituted (C$_1$-C$_{10}$)alkyl,
R$^2$ is (C$_1$-C$_{10}$)alkylene.
L is substituted or unsubstituted (C$_1$-C$_{10}$)alkylene or (C$_3$-C$_{10}$)cycloalkylene,
at least one of n and m is greater than or equal to 0, and the resin has an average molecular weight of less than 10,000 g/mol.

Embodiment 2 provides the resin of Embodiment 1, wherein m equal 0 and the resin of Formula I is:

Embodiment 4 provides the resin of any one of Embodiments 1-3, wherein the resin has a reduced potential to release phenolic compounds compared to corresponding resins comprising phenolic compounds, including bisphenols such as bisphenol A (BPA).

Embodiment 5 provides the resin of any one of Embodiments 1-4, wherein the resin is substantially free of repeating units derived from bisphenol A.

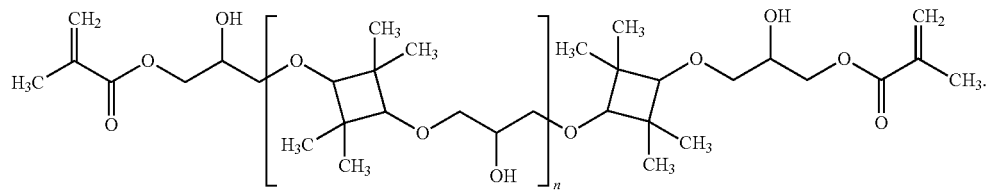

Embodiment 6 provides a method of making the Formula I of Embodiment 1, comprising:

reacting a resin according to Formula III:

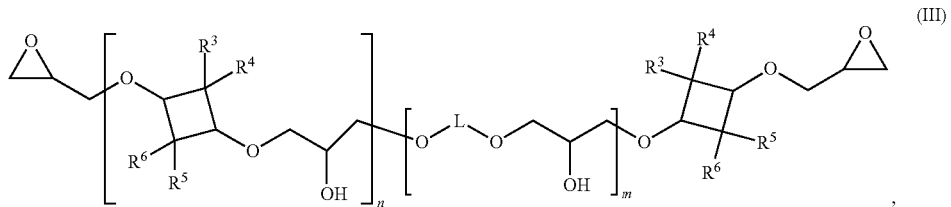

with a resin according to Formula IV:

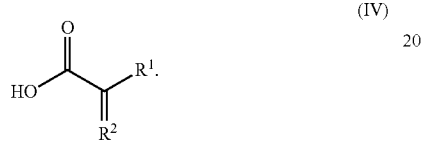

Embodiment 7 provides a method of making a resin according to Formula III of Embodiment 6, the method comprising:

reacting a molecule according to Formula V with a molecule according to Formula VI:

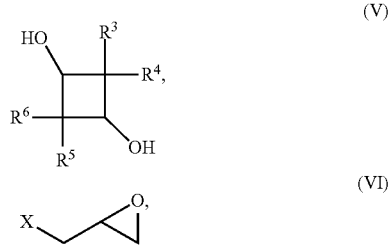

wherein X is selected from the group consisting of F, OH, Cl, Br, and I.

Embodiment 8 provides the method of Embodiment 6, wherein m equals 0 and Formula III is:

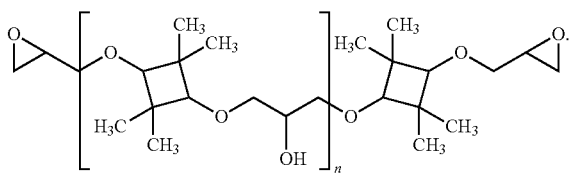

Embodiment 9 provides the method of Embodiment 6, wherein Formula IV is:

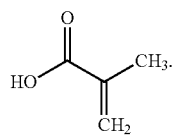

Embodiment 10 provides the method of Embodiment 7, wherein Formula V is:

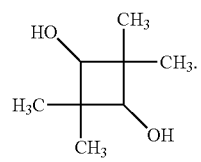

Embodiment 11 provides the method of Embodiment 7, wherein Formula VI is:

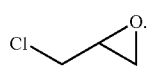

Embodiment 12 provides a cured product of a curable composition comprising at least one of Formula I and Formula II.

Embodiment 13 provides the cured product of Embodiment 12, wherein about 1 wt % to about 100 wt % of the curable composition is at least one of the structures according to Formula I and Formula II.

Embodiment 14 provides a method of forming the cured product according to Embodiment 12, comprising:

curing a curable composition comprising at least one of the structures according to Formula I and Formula II.

Embodiment 15 provides the method of forming the cured product of Embodiment 14, wherein the curable composition further comprises an initiator component.

Embodiment 16 provides the method of forming the cured product of Embodiment 15, wherein the initiator component ranges from about 0.1 wt % to about 25 wt % of the curable composition.

Embodiment 17 provides the method of forming the cured product of Embodiment 16, wherein the initiator is selected from methyl ethyl ketone peroxide, 2,4,6-trimethylbenzoyl-diphenylphosphine oxide, camphorquinone, benzoyl peroxide, phthaloyl peroxide, naphthoyl peroxide, alkyl- or alkanoyl-substituted peroxides such as acetyl, caproyl, lauroyl, tertiary butyl and di-t-butyl peroxides, alkyl-, alkanoyl- or chloro-substituted benzoyl peroxides such as acetyl benzoyl peroxide, dimethyl benzoyl peroxide and 2,4-dichlorobenzoyl peroxide, hydroperoxides such as di-isopropyl-benzene hydroperoxide, t-butyl hydroperoxide, and cumene hydroperoxide, and still other peroxides such as cinnamoyl peroxide, methyl ethyl ketone peroxide, 1-hydroxy-cyclohexyl-phenylketone, and 2,2-dimethoxy-2-phenylacetophenone, urea peroxide, alkali metal alkoxides, such as potassium, sodium or lithium methoxide, ethoxide, propoxide, isopropoxide, butoxide, or mixtures thereof.

Embodiment 18 provides the method of forming the cured product of any one of Embodiments 14-17, wherein the curable composition further comprises a reactive diluent.

Embodiment 19 provides the method of forming the cured product of Embodiment 18, wherein the reactive diluent ranges from about 0.01 wt % to about 70 wt % of the curable composition.

Embodiment 20 provides the method of forming the cured product of any one of Embodiments 18-19, wherein the reactive diluent is selected from styrene, triethylene glycol dimethacrylate, methyl methacrylate, butyl acrylate, butyl methacrylate, alpha methyl styrene, vinyl toluene, paramethyl styrene, diallyl phthalate, diallyl isophthalate, octyl acrylamide, trimethylol propane triacrylate, triallyl cyanurate, triallyl isocyanurate, diallyl malenate, diallyl tetrabromophtalate, ethyl methacrylate, n-propyl methacrylate, isopropyl methacrylate, n-butyl methacrylate, iso-butyl methacrylate, sec-butyl methacrylate, tert-butyl methacrylate, the amyl methacrylates, ethylene dimethacrylate, butylene dimethacrylate, ethylene glycol monomethacrylate, ethylene glycol dimethacrylate, diethylene glycol dimethacrylate, triethylene glycol dimethacrylate, tetraethylene glycol dimethacrylate, bis(glycidyl methacrylate) of 2,2,4,4-tetramethyl-1,3-cyclobutandiol and mixtures thereof.

Embodiment 21 provides the method of forming the cured product of any one of Embodiments 14-20, wherein the curable composition further comprises an accelerator.

Embodiment 22 provides the method of forming the cured product of Embodiment 21, wherein the accelerator ranges from about 0.001 wt % to about 5 wt % of the composition.

Embodiment 23 provides the method of forming the cured product of any one of Embodiments 21-22 wherein the accelerator is selected from cobalt naphthenate N,N-dimethylaniline, N, N-diethylaniline, 1,4-diazabicyclo[2.2.2]octane, 1,8-diazabicyclo[5.4.0]undec-7-ene, 1,5-diazabicyclo[4.3.0]non-5-ene, di-n-propylamine, n-hexylamine, or mixtures thereof.

Embodiment 24 provides the method of forming the cured product of any one of Embodiments 14-23, further comprising exposing the curable composition to visible or ultraviolet radiation.

Embodiment 25 provides the method of forming the cured product of any one of Embodiments 14-24, wherein the curable composition is cured at room temperature or higher.

Embodiment 26 provides the method of forming the cured product of Embodiment 25, further comprising increasing the temperature of the cured product to a temperature above a $T_g$ of the cured product but below a decomposition temperature of the cured product.

Embodiment 27 provides the method of forming the cured product of any one of Embodiments 14-25, further comprising depositing the curable composition on a tooth.

Embodiment 28 provides the method of forming the cured product of any of Embodiments 14-26, further comprising depositing the curable composition on a fiber.

Embodiment 29 provides the method of forming the cured product of any one of Embodiments 14-26, further comprising depositing the curable composition on a substrate.

Embodiment 30 provides a method of forming a dental sealant comprising forming the cured product of Embodiment 12.

What is claimed is:
1. A method of making a resin, comprising:
reacting a resin according to Formula III:

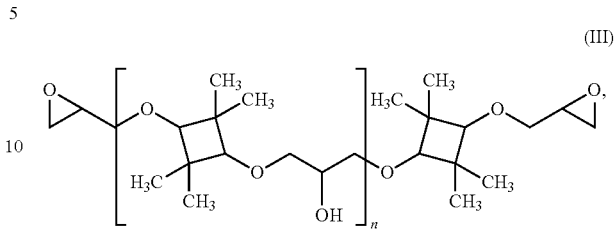

with a resin according to Formula IV:

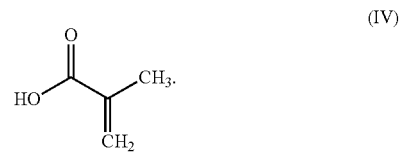

2. The resin of claim 1, wherein the resin has a reduced potential to release phenolic compounds compared to corresponding resins comprising bisphenol A (BPA).

3. The resin of claim 1, wherein the resin is substantially free of repeating units derived from bisphenol A.

4. A method of making a resin according to Formula III of claim 1, the method comprising:
reacting a molecule according to Formula V with a molecule according to Formula VI:

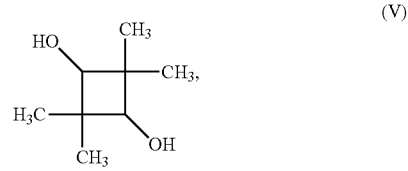

wherein X is selected from the group consisting of F, OH, Cl, Br, and I.

5. The method of claim 4, wherein Formula VI is:

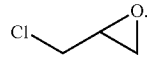

6. A cured product of a curable composition, the curable composition comprising a compound produced by the method of claim 1.

7. The cured product of claim 6, wherein about 1 wt % to about 100 wt % of the curable composition is the structures produced by the method of claim 1.

8. A method of forming the cured product according to claim 6, comprising:
curing a curable composition according to claim 6.

9. The method of forming the cured product of claim 8, wherein the curable composition further comprises an initiator component.

10. The method of forming the cured product of claim 9, wherein the initiator component ranges from about 0.1 wt % to about 25 wt % of the curable composition.

11. The method of forming the cured product of claim 8, wherein the curable composition further comprises a reactive diluent.

12. The method of forming the cured product of claim 11, wherein the reactive diluent ranges from about 0.01 wt % to about 70 wt % of the curable composition.

13. The method of forming the cured product of claim 8, wherein the curable composition further comprises an accelerator.

14. The method of forming the cured product of claim 8, further comprising exposing the curable composition to visible or ultraviolet radiation.

* * * * *